(12) United States Patent
DeGarlais

(10) Patent No.: US 11,628,289 B2
(45) Date of Patent: Apr. 18, 2023

(54) MEDICAL SYSTEM AND DISPOSABLE MEDICAL VACUUM DRAINAGE BAG FOR USE WITH SAME

(71) Applicant: Bard Peripheral Vascular, Inc., Franklin Lakes, NJ (US)

(72) Inventor: Netty DeGarlais, Gilbert, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 518 days.

(21) Appl. No.: 16/879,265

(22) Filed: May 20, 2020

(65) Prior Publication Data

US 2021/0361836 A1    Nov. 25, 2021

(51) Int. Cl.
*A61M 1/00*    (2006.01)
*A61M 39/22*   (2006.01)

(52) U.S. Cl.
CPC ..... *A61M 39/22* (2013.01); *A61M 2210/1007* (2013.01)

(58) Field of Classification Search
CPC .......... A61M 39/22; A61M 2210/1007; A61M 1/602; A61M 1/604; A61M 1/60; A61M 1/0011; A61M 1/0023; A61M 1/0001; A61M 1/00; A61B 2217/005; A61B 10/0283
See application file for complete search history.

(56) References Cited

U.S. PATENT DOCUMENTS

| | | |
|---|---|---|
| D330,427 S | 10/1992 | Meijer |
| 5,575,293 A | 11/1996 | Miller et al. |
| 6,695,791 B2 | 2/2004 | Gonzalez |
| 7,854,707 B2 | 12/2010 | Hibner et al. |
| 8,025,173 B2 * | 9/2011 | Michaels ............. A61M 1/604  220/495.08 |
| 8,034,003 B2 | 10/2011 | Pesce et al. |
| 8,118,755 B2 | 2/2012 | Hibner et al. |
| 8,702,623 B2 | 4/2014 | Parihar et al. |
| 9,877,706 B2 | 1/2018 | Speeg et al. |
| 10,071,190 B2 | 9/2018 | Hartwell et al. |
| 10,172,594 B2 | 1/2019 | Videbaek et al. |
| 10,201,331 B2 | 2/2019 | Fleming et al. |

(Continued)

FOREIGN PATENT DOCUMENTS

| | | | |
|---|---|---|---|
| WO | 2019156669 A1 | 8/2019 | |
| WO | WO-2019156669 A1 * | 8/2019 | ......... A61B 10/0096 |

*Primary Examiner* — Jason E Flick
(74) *Attorney, Agent, or Firm* — Dinsmore & Shohl LLP

(57) ABSTRACT

A disposable medical vacuum drainage bag includes a flexible enclosure made of a flexible material. The flexible enclosure is configured to define an interior chamber. The flexible enclosure has a first fluid port and a second fluid port. The flexible enclosure has a collapsed state and an expanded state. A framework is located in the interior chamber. The framework has a plurality of frame structures configured to rotate in unison about separate rotational axes between a collapsed configuration and an expanded configuration, wherein the collapsed configuration facilitates the collapsed state of the flexible enclosure and the expanded configuration facilitates the expanded state of the flexible enclosure. An actuator is coupled to the framework. The actuator is configured to rotatably transition the plurality of frame structures between the collapsed configuration and the expanded configuration.

20 Claims, 3 Drawing Sheets

(56) References Cited

U.S. PATENT DOCUMENTS

| | | |
|---|---|---|
| 10,413,280 B2 | 9/2019 | Speeg et al. |
| 2019/0059861 A1 | 2/2019 | Lough et al. |
| 2019/0099167 A1 | 4/2019 | Fleming et al. |
| 2019/0343493 A1 | 11/2019 | McCabe |
| 2021/0100936 A1* | 4/2021 | Whisler ......... A61B 17/320016 |

* cited by examiner

MEDICAL SYSTEM AND DISPOSABLE MEDICAL VACUUM DRAINAGE BAG FOR USE WITH SAME

CROSS-REFERENCE TO RELATED APPLICATIONS

None.

TECHNICAL FIELD

The present invention relates to a medical system that utilizes vacuum, and, more particularly, to a disposable medical vacuum drainage bag for use with the medical system.

BACKGROUND ART

Medical systems, such as a vacuum assisted breast biopsy system, may include a vacuum cannister that is located between the vacuum pump and the biopsy handpiece having the biopsy probe (needle). The vacuum cannister may be housed in a console of the breast biopsy system. Vacuum cannisters are notorious for air leaks, e.g., due to the difficulty in seating the lid on the vacuum cannister. Such air leaks result in a loss in vacuum (negative) pressure in the biopsy system, which in turn may adversely affect the ability to collect and transport a biopsy sample. Further, it may be difficult for clinicians to identify the source of the air leaks when troubleshooting the vacuum assisted biopsy system. Also, the volume of the vacuum canister is often overly large for the volume of fluid that is being aspirated in a typical breast biopsy procedure, and due to the large volume of the vacuum canister, it is quite possible for the vacuum canister to be used with multiple procedures.

What is needed in the art is a disposable medical vacuum drainage bag for use with a medical system that utilizes vacuum, such as for example, a vacuum assisted breast biopsy system.

SUMMARY OF INVENTION

The present invention provides a disposable medical vacuum drainage bag for use with a medical system that utilizes vacuum, such as for example, for use with a vacuum assisted breast biopsy system.

The invention, in one form, is directed to a disposable medical vacuum drainage bag that includes a flexible enclosure made of a flexible material. The flexible enclosure is configured to define an interior chamber. The flexible enclosure has a first fluid port and a second fluid port. The flexible enclosure has a collapsed state and an expanded state. A framework is located in the interior chamber. The framework has a plurality of frame structures configured to rotate in unison about separate rotational axes between a collapsed configuration and an expanded configuration, wherein the collapsed configuration facilitates the collapsed state of the flexible enclosure and the expanded configuration facilitates the expanded state of the flexible enclosure. An actuator is coupled to the framework. The actuator is configured to rotatably transition the plurality of frame structures between the collapsed configuration and the expanded configuration.

The invention, in another form, is directed to a medical system. The medical system includes a vacuum source, a medical device, and a disposable medical vacuum drainage bag. The medical device has a medical device vacuum port. The disposable medical vacuum drainage bag includes a flexible enclosure and a framework. The flexible enclosure is made of a flexible material. The flexible enclosure is configured to define an interior chamber. The flexible enclosure has a first fluid port coupled to the vacuum source and a second fluid port coupled to the medical device vacuum port of the medical device. The flexible enclosure has a collapsed state and an expanded state. The framework is located in the interior chamber. The framework has a plurality of frame structures configured to rotate in unison about separate rotational axes between a collapsed configuration and an expanded configuration, wherein the collapsed configuration facilitates the collapsed state of the flexible enclosure and the expanded configuration facilitates the expanded state of the flexible enclosure. An actuator is coupled to the framework. The actuator is configured to rotatably transition the plurality of frame structures between the collapsed configuration and the expanded configuration.

An advantage of the present invention is that the disposable medical vacuum drainage bag of the present invention is configured to transition between a collapsed (e.g., flattened) state/configuration and an expanded (e.g., usage) state/configuration, wherein the collapsed (e.g., flattened) state of the disposable medical vacuum drainage bag requires less storage space than that of a traditional vacuum cannister, and the expanded (e.g., usage) state of the disposable medical vacuum drainage bag maintains a vacuum/fluid path through the disposable medical vacuum drainage bag.

Another advantage of the present invention is that the disposable medical vacuum drainage bag of the present invention provides improved vacuum reliability, e.g., less vacuum leaks, over that of a traditional vacuum cannister.

Another advantage of the present invention is that the disposable medical vacuum drainage bag of the present invention provides ease of use, by simply being connectably interposed in the vacuum path between the vacuum source and the vacuum assisted medical device (e.g., a vacuum assisted biopsy device).

Another advantage of the present invention is that the disposable medical vacuum drainage bag of the present invention provides reduced risk of re-use over that of a traditional vacuum cannister, because the disposable medical vacuum drainage bag of the present invention is easily removable and sealable after use, and is intended to be disposed of after a single use.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
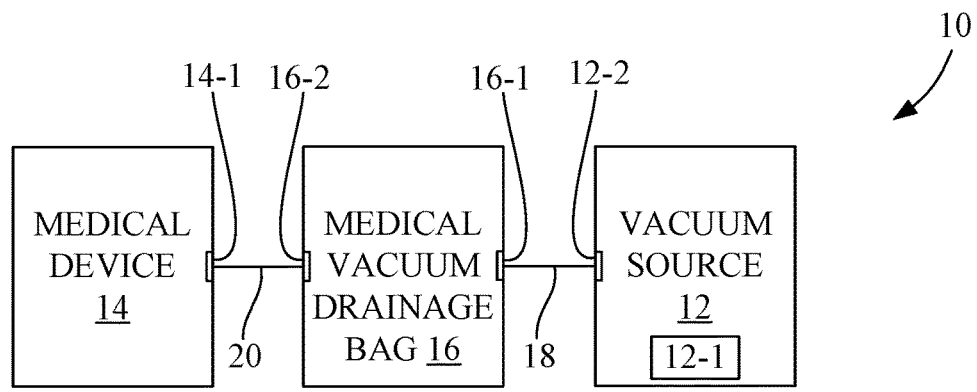
FIG. 1 is a block diagram of a medical system having a vacuum source and a medical device, and having a disposable medical vacuum drainage bag in accordance with an aspect of the present invention.

Referring now to the drawings, and more particularly to FIG. 1, there is shown a medical system 10 which generally includes a vacuum source 12, a medical device 14, and a disposable medical vacuum drainage bag 16 in accordance with an aspect of the present invention. Medical system 10 may be, for example, a vacuum assisted breast biopsy system, wherein disposable medical vacuum drainage bag 16 replaces, or supplements, the traditional vacuum cannister of an existing vacuum assisted breast biopsy system. Such existing vacuum assisted breast biopsy systems that may be adapted to use disposable medical vacuum drainage bag 16 may include, for example, the EnCor Enspire™ and the EnCor Ultra™ brand vacuum assisted breast biopsy systems available from BD-Bard, having an office in Tempe, Ariz.

Vacuum source 12 is a source of negative pressure. Vacuum source 12 may include, for example, a vacuum pump 12-1 and a vacuum source port 12-2. Vacuum pump 12-1 may be, for example, a piston pump or a diaphragm pump. Vacuum source port 12-2 of vacuum source 12 is connected in fluid communication with a first fluid port 16-1 of disposable medical vacuum drainage bag 16 via a fluid conduit 18. Fluid conduit 18 may be, for example, a flexible rubber hose.

Medical device 14 is a device used by a medical professional for performing a medical procedure. Medical device 14 may be, for example, a biopsy device, such as the palm-sized handpiece and biopsy probe combination utilized in the EnCor Enspire™ or EnCor Ultra™ brand vacuum assisted breast biopsy systems available from BD/Bard. Medical device 14 has a medical device vacuum port 14-1 that is connected in fluid communication with a second fluid port 16-2 of disposable medical vacuum drainage bag 16 via a fluid conduit 20. Fluid conduit 20 may be, for example, a flexible rubber hose.

Figure 2:
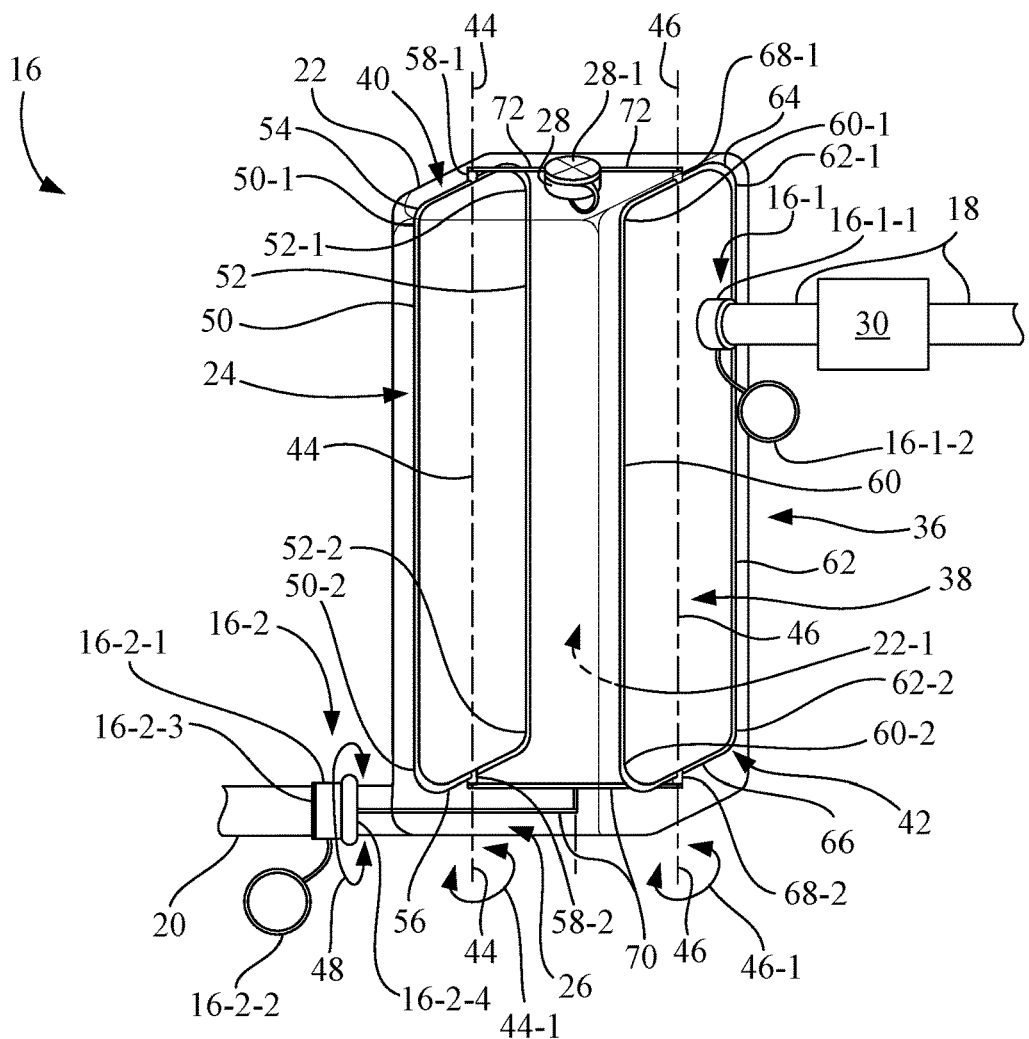
FIG. 2 is a perspective pictorial representation of the disposable medical vacuum drainage bag of FIG. 1 having a flexible enclosure and an internal framework, with the flexible enclosure being in an expanded (e.g., usage) state as facilitated by the internal framework being in an expanded configuration.
Figure 3:
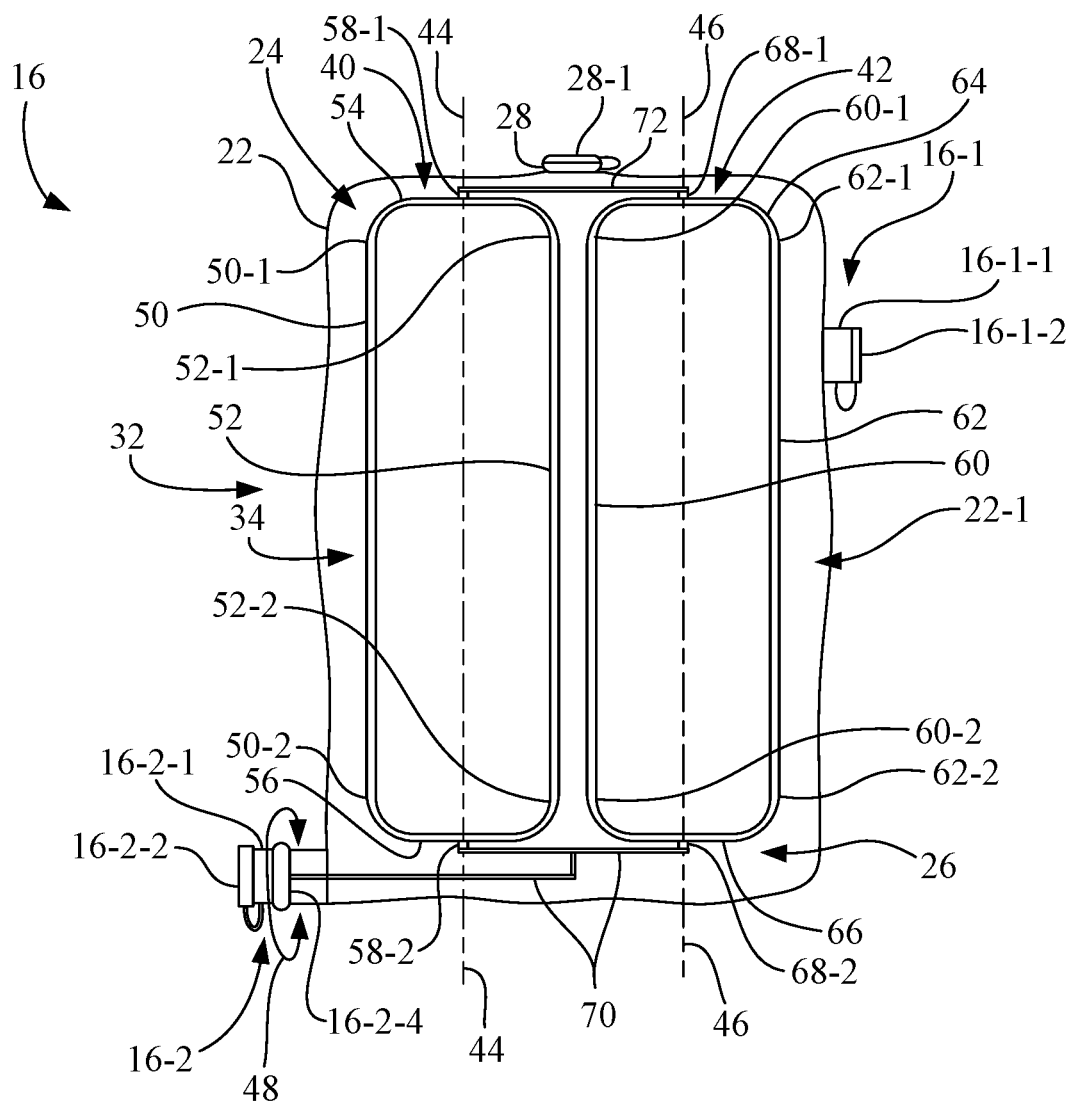
FIG. 3 is a side view of the pictorial representation of the disposable medical vacuum drainage bag of FIG. 2, with the flexible enclosure being in a collapsed (e.g., storage) state as facilitated by the internal framework being in a collapsed configuration.
Figure 4:
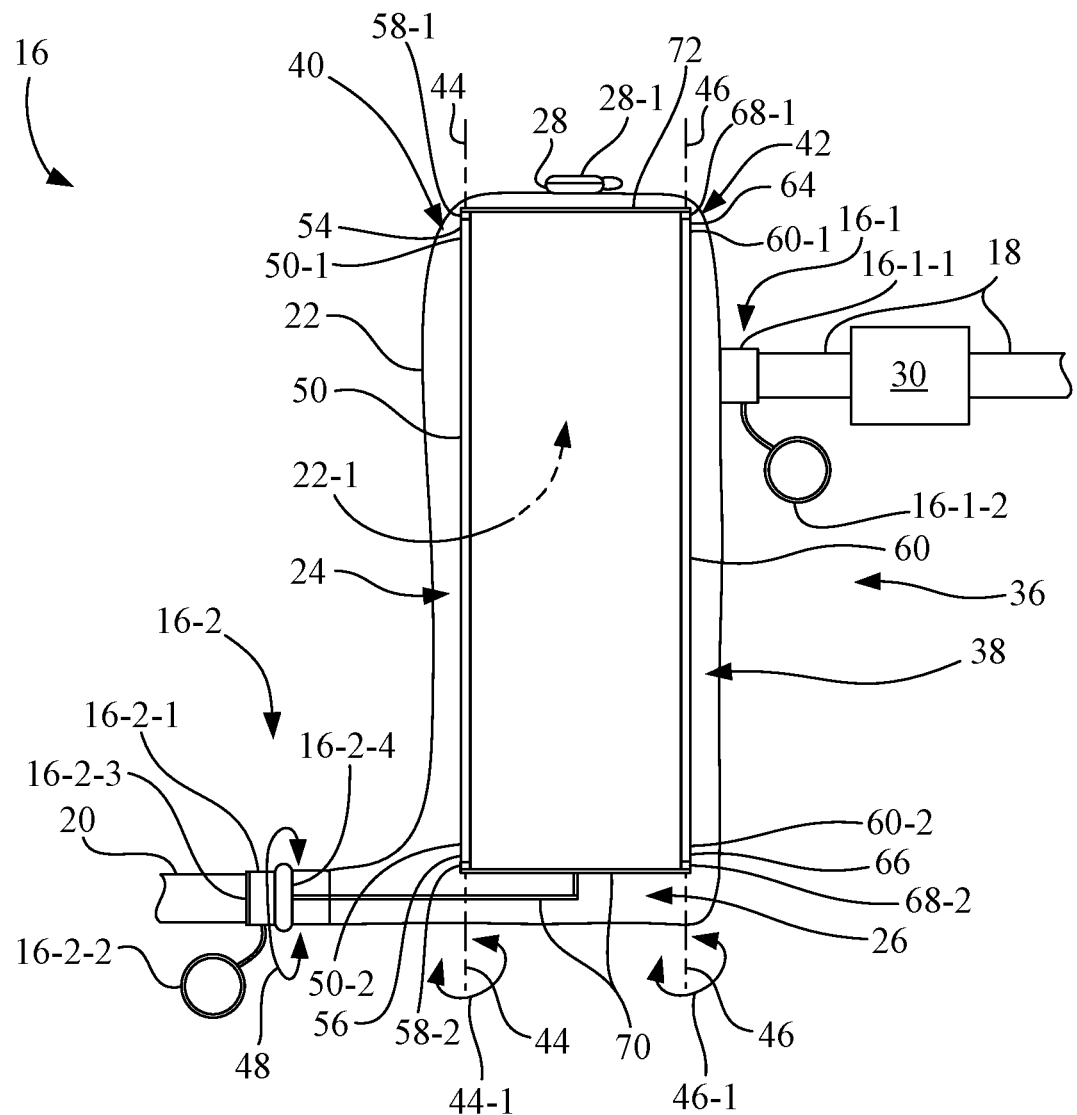
FIG. 4 is a side view of the pictorial representation of the disposable medical vacuum drainage bag of FIG. 2, with the flexible enclosure being in the expanded (e.g., usage) state as facilitated by the internal framework being in the expanded configuration.

Referring also to FIGS. 2-4, disposable medical vacuum drainage bag 16 includes a flexible enclosure 22, a framework 24, and an actuator 26.

Flexible enclosure 22 is made of a flexible material, such as a flexible plastic bag, flexible silicone bag, etc. Flexible enclosure 22 is configured to define an interior chamber 22-1. Framework 24 is located in interior chamber 22-1 of flexible enclosure 22 of disposable medical vacuum drainage bag 16.

First fluid port 16-1 of disposable medical vacuum drainage bag 16 is mechanically connected to flexible enclosure 22 and is coupled in fluid communication with interior chamber 22-1 of flexible enclosure 22. Likewise, second fluid port 16-2 of disposable medical vacuum drainage bag 16 is mechanically connected to flexible enclosure 22 and is coupled in fluid communication with interior chamber 22-1 of flexible enclosure 22. Accordingly, first fluid port 16-1 of flexible enclosure 22 of disposable medical vacuum drainage bag 16 may be coupled to vacuum source port 12-2 of vacuum source 12 via fluid conduit 18, and second fluid port 16-2 of flexible enclosure 22 of disposable medical vacuum drainage bag 16 may be coupled to medical device vacuum port 14-1 of medical device 14 via fluid conduit 20.

First fluid port 16-1 of disposable medical vacuum drainage bag 16 may include a connector 16-1-1 and removable cap 16-1-2. In the present embodiment, removable cap 16-1-2 is tethered to connector 16-1-1. Connector 16-1-1 is configured, e.g., as a Luer fitting or a threaded fitting, to be connectable to vacuum source port 12-2 of vacuum source 12 via fluid conduit 18. Removable cap 16-1-2, e.g., of a screw-on type or snap-fit type, may be engaged with connector 16-1-1 so as to seal first fluid port 16-1 when first fluid port 16-1 is disconnected from fluid conduit 18.

Second fluid port 16-2 of disposable medical vacuum drainage bag 16 may include a connector 16-2-1, removable cap 16-2-2, a one-way fluid valve 16-2-3, and a rotatable collar 16-2-4. In the present embodiment, removable cap 16-2-2 is tethered to connector 16-2-1. Connector 16-2-1 is configured, e.g., as a Luer fitting or a threaded fitting, to be connectable to medical device vacuum port 14-1 of medical device 14 via fluid conduit 20. Removable cap 16-2-2, e.g., of a screw-on type or snap-fit type, may be engaged with connector 16-2-1 so as to seal second fluid port 16-2 when second fluid port 16-2 is disconnected from fluid conduit 20. One-way fluid valve 16-2-3, e.g., a check-valve, is configured to define a one-way fluid flow in a direction from the connector 16-2-1 toward interior chamber 22-1 of flexible enclosure 22, so as to prevent a backflow of fluid from disposable medical vacuum drainage bag 16 toward medical device 14.

Rotatable collar 16-2-4 of second fluid port 16-2 of disposable medical vacuum drainage bag 16 forms an external portion of actuator 26, and thus, is positioned outside flexible enclosure 22 to be operably rotated, e.g., in bidirectional directions 48, by a user, e.g., a clinician. Rotatable collar 16-2-4 is operably coupled by actuator 26 to framework 24 so as to transition framework 24 between multiple configurations, as further described below.

Optionally, disposable medical vacuum drainage bag 16 also may include a vent port 28 that is mechanically connected to flexible enclosure 22, and wherein vent port 28 is coupled in fluid communication with interior chamber 22-1. Vent port 28 may include a removable cap 28-1, e.g., of a screw-on type or snap-fit type, that may be removed or loosened to vent interior chamber 22-1 to the atmosphere surrounding the exterior of flexible enclosure 22 of disposable medical vacuum drainage bag 16. In the present embodiment, removable cap 28-1 is tethered to vent port 28.

As shown in FIG. 2, optionally, a biological filter 30 may be installed in fluid conduit 18 between vacuum source 12 and disposable medical vacuum drainage bag 16, so as to prevent biological material, e.g., blood, from entering and contaminating vacuum source 12.

Referring to FIG. 3, flexible enclosure 22 has a collapsed state 32, e.g., a flattened state, wherein the volume of interior chamber 22-1 is minimized by a collapsed configuration 34 (e.g., a flattened configuration) of framework 24. Referring to FIGS. 2 and 4, flexible enclosure 22 has an expanded state 36, e.g., akin to an inflated state, wherein the volume of interior chamber 22-1 is increased by an expanded configuration 38 of framework 24. Accordingly, interior chamber 22-1 of flexible enclosure 22 of disposable medical vacuum drainage bag 16 has a variable volume that is variable depending upon a particular configuration of framework 24.

Collapsed state 32 of flexible enclosure 22 and collapsed configuration 34 (e.g., flattened configuration) of framework 24, of disposable medical vacuum drainage bag 16, is useful in situations where it is desirable to minimize the space (volume) taken up by disposable medical vacuum drainage bag 16. For example, it may be desirable to minimize the space taken up by disposable medical vacuum drainage bag 16 during storage, packaging, and/or shipping of disposable medical vacuum drainage bag 16.

Expanded state 36 of flexible enclosure 22, as realized and effected by the expanded configuration 38 (e.g., a box-like arrangement) of framework 24, represents the state in which disposable medical vacuum drainage bag 16 is used during a medical procedure. For example, when flexible enclosure 22 is placed in expanded state 36 by framework 24, framework 24 prevents flexible enclosure 22 from totally collapsing on itself during the application of vacuum (negative pressure) by vacuum source 12. Accordingly, when flexible enclosure 22 is in expanded state 36, framework 24 maintains an open passage between first fluid port 16-1 and second fluid port 16-2 of disposable medical vacuum drainage bag 16, and maintains an amount of volume in interior chamber 22-1 of flexible enclosure 22 of disposable medical vacuum drainage bag 16, so as to facilitate a free flow of fluid, e.g., air, biological fluids (e.g., blood), and aspiration liquids (e.g., saline), into disposable medical vacuum drainage bag 16 in a direction from medical device 14 toward vacuum source 12.

As shown in FIGS. 2-4, framework 24 is located in interior chamber 22-1. Framework 24 has a plurality of frame structures (i.e., two or more frame structures; also referenced as 24) that, in the present embodiment, are individually identified as a first frame structure 40 and a second frame structure 42. In the present embodiment, first frame structure 40 and second frame structure 42 may be configured to be substantially identical in form and function. The plurality of frame structures 24 are configured to rotate in unison about separate rotational axes between collapsed configuration 34 (see FIG. 3) and expanded configuration 38 (see FIGS. 2 and 4).

In the present embodiment, first frame structure 40 is configured to rotate about a first rotational axis 44, e.g., in bidirectional directions 44-1, and second frame structure 42 is configured to rotate about a second rotational axis 46, e.g., in bidirectional directions 46-1. Collapsed configuration 34 of the plurality of frame structures 24 (e.g., of first frame structure 40 and second frame structure 42) facilitates collapsed state 32 of flexible enclosure 22, and expanded configuration 38 of the plurality of frame structures 24 (e.g., of first frame structure 40 and second frame structure 42) facilitates expanded state 36 of flexible enclosure 22. A rotational extent of each of first frame structure 40 and second frame structure 42 from collapsed configuration 34 to achieve expanded configuration 38 may be, for example, approximately 90 degrees of rotation, e.g., 90 degrees plus or minus 10 degrees.

In the present embodiment, first frame structure 40 includes a first elongate section member 50, a second elongate section member 52, a first bridge section member 54, and a second bridge section member 56 that are arranged to form a unitary planar frame, which in the present embodiment may be a unitary planar open frame. Each of first elongate section member 50, second elongate section member 52, first bridge section member 54, and second bridge section member 56 may be formed, for example, from a plastic rod or a plastic tube. In one embodiment, for example, a single continuous plastic rod or a plastic tube may be used to form first elongate section member 50, second elongate section member 52, first bridge section member 54, and second bridge section member 56 as a single piece unitary structure.

First elongate section member 50 has a first proximal end 50-1 and a first distal end 50-2. Second elongate section member 52 has a second proximal end 52-1 and a second distal end 52-2. First bridge section member 54 is connected to, and is interposed between, first proximal end 50-1 of first elongate section member 50 and second proximal end 52-1 of second elongate section member 52. Second bridge section member 56 is connected to, and interposed between, first distal end 50-2 of first elongate section member 50 and second distal end 52-2 of second elongate section member 52.

First bridge section member 54 may be configured to be curved, e.g., having a curved radius at opposed ends of first bridge section member 54. Likewise, second bridge section member 56 may be configured to be curved, e.g., having a curved radius at opposed ends of first bridge section member 54.

First bridge section member 54 of first frame structure 40 has a first (e.g., upper) rotational axle 58-1. Second bridge section member 56 of first frame structure 40 has a second (e.g., lower) rotational axle 58-2. First rotational axle 58-1 and second rotational axle 58-2 of first frame structure 40 are coaxially arranged along first rotational axis 44 for rotation about first rotational axis 44 between collapsed configuration 34 (see FIG. 3) and expanded configuration 38 (see FIGS. 2 and 4).

In the present embodiment, second frame structure 42 includes a first elongate section member 60, a second elongate section member 62, a first bridge section member 64, and a second bridge section member 66 that are arranged to form a unitary planar frame, which in the present embodiment may be a unitary planar open frame. Each of first elongate section member 60, second elongate section member 62, first bridge section member 64, and second bridge section member 66 may be formed, for example, from a plastic rod or a plastic tube. In one embodiment, for example, a single continuous plastic rod or a plastic tube may be used to form first elongate section member 60, second elongate section member 62, first bridge section member 64, and second bridge section member 66 as a single piece unitary structure.

First elongate section member 60 of second frame structure 42 has a first proximal end 60-1 and a first distal end 60-2. Second elongate section member 62 of second frame structure 42 has a second proximal end 62-1 and a second distal end 62-2. First bridge section member 64 is connected to, and is interposed between, first proximal end 60-1 of first elongate section member 60 and second proximal end 62-1 of second elongate section member 62. Second bridge section member 66 is connected to, and interposed between, first distal end 60-2 of first elongate section member 60 and second distal end 62-2 of second elongate section member 62.

First bridge section member 64 of second frame structure 42 may be configured to be curved, e.g., having a curved radius at opposed ends of first bridge section member 64. Likewise, second bridge section member 66 of second frame structure 42 may be configured to be curved, e.g., having a curved radius at opposed ends of first bridge section member 64.

First bridge section member 64 of second frame structure 42 has a first rotational axle 68-1. Second bridge section member 66 of second frame structure 42 has a second rotational axle 68-2. First rotational axle 68-1 and second rotational axle 68-2 of second frame structure 42 are coaxially arranged along second rotational axis 46 for rotation about second rotational axis 46 between collapsed configuration 34 (see FIG. 3) and expanded configuration 38 (see FIGS. 2 and 4).

Actuator 26 is coupled to framework 24 (i.e., to the plurality of frame structures 24). In the present embodiment, for example, actuator 26 is coupled to each of first frame structure 40 and second frame structure 42. Actuator 26 is configured to rotatably transition the plurality of frame structures 24 between collapsed configuration 34 (see FIG. 3) and expanded configuration 38 (see FIGS. 2 and 4).

In the present embodiment, actuator 26 includes a linkage member 70, the rotatable collar 16-2-4 of second fluid port 16-2, and a cross-link member 72. Linkage member 70 may be located, at least in part, in interior chamber 22-1 of flexible enclosure 22. Cross-link member 72 may be located, e.g., in its entirety, in interior chamber 22-1 of flexible enclosure 22. Rotatable collar 16-2-4 is operably connected to linkage member 70, which together are configured to operably transition framework 24 between collapsed configuration 34 (see FIG. 3) and expanded configuration 38 (see FIGS. 2 and 4) upon rotation of rotatable collar 16-2-4 in one of bidirectional directions 48, by the user, e.g., the clinician.

Cross-link member 72 is configured, e.g., with opposed bearing ends, to passively align first rotational axle 58-1 of first frame structure 40 along first rotational axis 44, and to passively align first rotational axle 68-1 of second frame structure 42 along second rotational axis 46. In other words, cross-link member 72 provides a fixed lateral spacing between first rotational axle 58-1 of first frame structure 40 and first rotational axle 68-1 of second frame structure 42, and permits the rotation of first frame structure 40 about first rotational axis 44 and the rotation of second frame structure 42 about second rotational axis 46.

Linkage member 70 is configured, e.g., with a drivetrain formed by respective drive members, such as shafts and gears, to actively align second rotational axle 58-2 of first frame structure 40 along first rotational axis 44 and to actively align second rotational axle 68-2 of second frame structure 42 along second rotational axis 46. In other words, linkage member 70 provides a fixed lateral spacing between second rotational axle 58-2 of first frame structure 40 and second rotational axle 68-2 of second frame structure 42, and also receives and transfers a motive force, e.g., via the drivetrain, from rotatable collar 16-2-4 to simultaneously (i.e., in unison) rotate first frame structure 40 about first rotational axis 44 and rotate second frame structure 42 about second rotational axis 46.

Accordingly, in the present embodiment, rotatable collar 16-2-4 is operably coupled to framework 24 via linkage member 70, and linkage member 70 is connected to each of first frame structure 40 and second frame structure 42. For example, each of second rotational axle 58-2 of first frame structure 40 and second rotational axle 68-2 of second frame structure 42 is operably coupled to linkage member 70 so as to effect simultaneous rotation of first frame structure 40 and second frame structure 42 between collapsed configuration 34 (see FIG. 3) and expanded configuration 38 (see FIGS. 2 and 4) by rotation of rotatable collar 16-2-4. In the present embodiment, for example, rotatable collar 16-2-4 is rotatably coupled to linkage member 70, and linkage member 70 is configured and arranged to rotate second rotational axle 58-2 of first frame structure 40 about first rotational axis 44 and to rotate second rotational axle 68-2 of second frame structure 42 about second rotational axis 46.

Stated differently, linkage member 70 is configured to rotate, in unison, first frame structure 40 about first rotational axis 44 and second frame structure 42 about second rotational axis 46, wherein linkage member 70 is configured to be actuated by rotatable collar 16-2-4 to effect the transition of first frame structure 40 and second frame structure 42 between collapsed configuration 34 (see FIG. 3) and expanded configuration 38 (see FIGS. 2 and 4) upon rotation of the rotatable collar 16-2-4.

As used herein, the terms "approximately", "substantially", and other words of degree are relative modifiers intended to indicate permissible variation from the characteristic so modified. Such terms are not intended to be limited to the absolute value of the characteristic which it modifies, but rather possessing more of the physical or functional characteristic than the opposite, and approaching such a physical or functional characteristic.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A disposable medical vacuum drainage bag, comprising:
   a flexible enclosure made of a flexible material, the flexible enclosure configured to define an interior chamber, the flexible enclosure having a first fluid port and a second fluid port, the flexible enclosure having a collapsed state and an expanded state;
   a framework located in the interior chamber, the framework having a plurality of frame structures configured to rotate in unison about separate rotational axes between a collapsed configuration and an expanded configuration, wherein the collapsed configuration facilitates the collapsed state of the flexible enclosure and the expanded configuration facilitates the expanded state of the flexible enclosure; and
   an actuator coupled to the framework, the actuator configured to rotatably transition the plurality of frame structures between the collapsed configuration and the expanded configuration.

2. The disposable medical vacuum drainage bag of claim 1, wherein the plurality of frame structures includes a first frame structure and a second frame structure, the first frame structure having a first rotational axis and the second frame structure having a second rotational axis, and wherein the actuator is coupled to each of the first frame structure and the second frame structure.

3. The disposable medical vacuum drainage bag of claim 2, wherein the actuator includes a linkage member and a rotatable collar rotatably coupled to the linkage member, the linkage member being connected to each of a first frame structure and a second frame structure, the linkage member configured to rotate, in unison, the first frame structure about the first rotational axis and the second frame structure about the second rotational axis, the linkage member configured to be actuated by the rotatable collar to effect the transition of the first frame structure and the second frame structure between the collapsed configuration and the expanded configuration upon rotation of the rotatable collar.

4. The disposable medical vacuum drainage bag of claim 3, wherein a rotational extent of each of the first frame structure and the second frame structure from the collapsed configuration to the expanded configuration is approximately 90 degrees of rotation.

5. The disposable medical vacuum drainage bag of claim 1, wherein the second fluid port comprises:
   a connector configured to be connectable to a medical device vacuum port of a medical device;
   a one-way fluid valve configured to define a one-way fluid flow in a direction from the connector toward the interior chamber of the flexible enclosure; and
   a rotatable collar coupled to the framework, and wherein the actuator comprises the rotatable collar, the rotatable collar configured to transition the framework between the collapsed configuration and the expanded configuration upon rotation of the rotatable collar.

6. The disposable medical vacuum drainage bag of claim 5, wherein the first fluid port is configured to be connectable to a vacuum source.

7. The disposable medical vacuum drainage bag of claim 1, wherein each frame structure of the plurality of frame structures includes:
   a first elongate section member having a first proximal end and a first distal end;
   a second elongate section member having a second proximal end and a second distal end;
   a first bridge section member connected to, and interposed between, the first proximal end of the first elongate section member and the second proximal end of the second elongate section member; and
   a second bridge section member connected to, and interposed between, the first distal end of the first elongate section member and the second distal end of the second elongate section member.

8. The disposable medical vacuum drainage bag of claim 7, wherein the first elongate section member, the second elongate section member, the first bridge section member, and the second bridge section member are arranged to form a unitary planar frame.

9. The disposable medical vacuum drainage bag of claim 7, wherein at least one of the first bridge section member and the second bridge section member is curved.

10. The disposable medical vacuum drainage bag of claim 7, wherein each of the first elongate section member, the second elongate section member, the first bridge section member, and the second bridge section member is formed from a plastic rod or a plastic tube.

11. A medical system, comprising:
    a vacuum source;
    a medical device having a medical device vacuum port; and
    a disposable medical vacuum drainage bag that includes:
      a flexible enclosure made of a flexible material, the flexible enclosure configured to define an interior chamber, the flexible enclosure having a first fluid port coupled to the vacuum source and a second fluid port coupled to the medical device vacuum port of the medical device and, the flexible enclosure having a collapsed state and an expanded state;
      a framework located in the interior chamber, the framework having a plurality of frame structures configured to rotate in unison about separate rotational axes between a collapsed configuration and an expanded configuration, wherein the collapsed configuration facilitates the collapsed state of the flexible enclosure and the expanded configuration facilitates the expanded state of the flexible enclosure; and
      an actuator coupled to the framework, the actuator configured to rotatably transition the plurality of frame structures between the collapsed configuration and the expanded configuration.

12. The medical system of claim 11, wherein the plurality of frame structures includes a first frame structure and a second frame structure, the first frame structure having a first rotational axis and the second frame structure having a second rotational axis, and wherein the actuator is coupled to each of the first frame structure and the second frame structure.

13. The medical system of claim 12, wherein the actuator includes a linkage member and a rotatable collar rotatably coupled to the linkage member, the linkage member being connected to each of a first frame structure and a second frame structure, the linkage member configured to rotate, in unison, the first frame structure about the first rotational axis and the second frame structure about the second rotational axis, the linkage member configured to be actuated by the rotatable collar to effect the transition of the first frame structure and the second frame structure between the collapsed configuration and the expanded configuration upon rotation of the rotatable collar.

14. The medical system of claim 13, wherein a rotational extent of each of the first frame structure and the second frame structure from the collapsed configuration to the expanded configuration is approximately 90 degrees of rotation.

15. The medical system of claim 11, wherein the second fluid port comprises:
    a connector configured to be connectable to the medical device vacuum port of a medical device;
    a one-way fluid valve configured to define a one-way fluid flow in a direction from the connector toward the interior chamber of the flexible enclosure; and
    a rotatable collar coupled to the framework, and wherein the actuator comprises the rotatable collar, the rotatable collar configured to transition the framework between the collapsed configuration and the expanded configuration upon rotation of the rotatable collar.

16. The medical system of claim 15, wherein the flexible enclosure is a flexible plastic bag or a flexible silicone bag.

17. The medical system of claim 11, wherein each frame structure of the plurality of frame structures includes:
    a first elongate section member having a first proximal end and a first distal end;
    a second elongate section member having a second proximal end and a second distal end;
    a first bridge section member connected to, and interposed between, the first proximal end of the first elongate section member and the second proximal end of the second elongate section member; and
    a second bridge section member connected to, and interposed between, the first distal end of the first elongate section member and the second distal end of the second elongate section member.

18. The medical system of claim 17, wherein the first elongate section member, the second elongate section member, the first bridge section member, and the second bridge section member are arranged to form a unitary planar frame.

19. The medical system of claim 17, wherein at least one of the first bridge section member and the second bridge section member is curved.

20. The medical system of claim 17, wherein each of the first elongate section member, the second elongate section member, the first bridge section member, and the second bridge section member is formed from a plastic rod or a plastic tube.

\* \* \* \* \*